(12) United States Patent
Lin et al.

(10) Patent No.: US 11,801,337 B2
(45) Date of Patent: Oct. 31, 2023

(54) MEDICAL DEVICE

(71) Applicant: Clearmind Biomedical, Inc., San Jose, CA (US)

(72) Inventors: Sheng Chi Lin, Hsinchu (TW); Feng-cheng Chang, Taipei (TW); Yu Jen Lin, Taipei (TW)

(73) Assignee: Clearmind Biomedical Inc., San Jose, CA (US)

( * ) Notice: Subject to any disclaimer, the term of this patent is extended or adjusted under 35 U.S.C. 154(b) by 143 days.

(21) Appl. No.: 17/566,487

(22) Filed: Dec. 30, 2021

(65) Prior Publication Data

US 2023/0211064 A1   Jul. 6, 2023

(51) Int. Cl.
| | |
|---|---|
| *A61M 1/00* | (2006.01) |
| *A61B 90/00* | (2016.01) |
| *A61B 18/00* | (2006.01) |
| *A61B 18/14* | (2006.01) |

(52) U.S. Cl.
CPC ............. *A61M 1/743* (2021.05); *A61B 18/14* (2013.01); *A61B 90/361* (2016.02); *A61B 2018/00595* (2013.01); *A61B 2018/1412* (2013.01); *A61B 2218/007* (2013.01); *A61M 1/76* (2021.05)

(58) Field of Classification Search
CPC . A61B 1/00068; A61B 1/015; A61B 1/00066; A61B 1/0052; A61B 2217/005; A61B 2217/007; A61B 17/2909; A61B 17/3498; A61B 17/32; A61B 18/00; A61B 2018/00916; A61B 2018/0091; A61B 2017/00137; A61B 1/00064; A61B 1/12; A61M 1/774; A61M 1/743; A61M 1/76; A61M 1/741; A61M 1/7413; A61M 25/0136; A61M 39/22; A61M 3/0283; A61F 9/007

See application file for complete search history.

(56) References Cited

U.S. PATENT DOCUMENTS

| | | | |
|---|---|---|---|
| 6,652,488 B1 * | 11/2003 | Cover ................... | A61M 1/774 604/32 |
| 2003/0106559 A1 * | 6/2003 | Svendsen .......... | A61M 16/0816 128/207.14 |
| 2007/0106204 A1 * | 5/2007 | Fedenia ................ | A61M 1/772 604/28 |

FOREIGN PATENT DOCUMENTS

WO   WO-2020160434 A1 *  8/2020 ......... A61F 9/00736

\* cited by examiner

*Primary Examiner* — Erich G Herbermann
*Assistant Examiner* — Linnae E. Raymond
(74) *Attorney, Agent, or Firm* — Wissing Miller LLP

(57) ABSTRACT

The present patent specification provides a medical device including an outer tube, an operation portion and a control portion. The operation portion is at least partially located in the outer tube. The control portion has a channel communicating with the outer tube along a first direction; a second end of the control portion is coupled with a first end of the outer tube so that the channel and the outer tube communicate with each other along the first direction. The control portion includes a control module including a suction control unit, a suction, a suction valve actuator and a switching unit. The suction control unit has a stopping unit and is configured to move along a second direction which is different from the first direction. The suction valve actuator is located at a side opposite the suction control unit with the channel therebetween and the suction valve actuator is configured to be activated by the suction control unit. The switching unit is configured to switch the work status of the operation portion.

13 Claims, 11 Drawing Sheets

MEDICAL DEVICE

1. FIELD

The present disclosure relates to a medical device; specifically, the present disclosure relates to a medical device which can perform suction, flush and debridement without replacing equipment.

2. BACKGROUND

In traditional surgeries, the use of suction/flush devices to reduce liquid waste that result in low visibility of tissues, endoscopes to view the inside of tissues, and debridement devices to remove devitalized tissues can require the use of both hands and the need to replace devices frequently. As a result, a surgeon's job becomes more complex.

In addition, in order to perform cautery, the cautery device needs to be inserted after removing the debridement devices or suction/flush devices; hence, the operational procedures for surgeons are more complex.

Therefore, an ideal set up would include a single medical device that has multiple functions so as to decrease the frequency of the surgeon replacing surgical instruments and to ensure the safety of the patient receiving surgical treatment.

SUMMARY

The present disclosure intends to provide a medical device which is convenient for surgeons to use and has safety activation mechanisms.

The present disclosure provides a medical device including an outer tube, an operation portion, and a control portion. The control portion has a channel communicating with the outer tube along a first direction. The control portion includes a control module, and the control module includes a suction control portion, a suction port actuator, and a switching unit. The suction control portion has a stopping unit toward the channel, and is configured to move along a second direction which is different from the channel. The suction valve actuator is located at the side opposite to the suction control portion with the channel therebetween and driven by the suction control portion. The switching unit is configured to be released and driven by the suction control portion to switch the work status of the operation unit.

When the suction control portion is located at the first position, the control module is configured to stop the suction port actuator from creating suction in the channel and the switching unit is configured to stop the activation of the operation unit.

When the suction control portion is located at the second position, the control module is configured to enable the suction port actuator to create suction in the channel.

When the suction control portion is located at the third position, the control module is configured to enable the suction port actuator to create suction in the channel and drive the switching unit to activate the operation portion. In addition, the stopping unit at least partially extends into the channel.

Through the mentioned configuration, a single medical device can perform multiple tasks; specifically, it can perform debridement at the same time as drawing blood so as to ensure good visibility during the process of surgery. In addition, the suction control portion is further prevented from moving from the second position to the third position by using the combination of the stopping unit and an external device.

DETAILED DESCRIPTION

The various embodiments will be described in detail below so persons skilled in the art may understand the advantages and effects of the present disclosure through the contents disclosed in the present specification with reference to the accompanying drawing. However, the contents below do not limit the scope of the present disclosure. Without departing from the principles of the present invention, a person having ordinary skill in the present art may realize the present disclosure through other embodiments based on different views and applications.

Figure 1A:
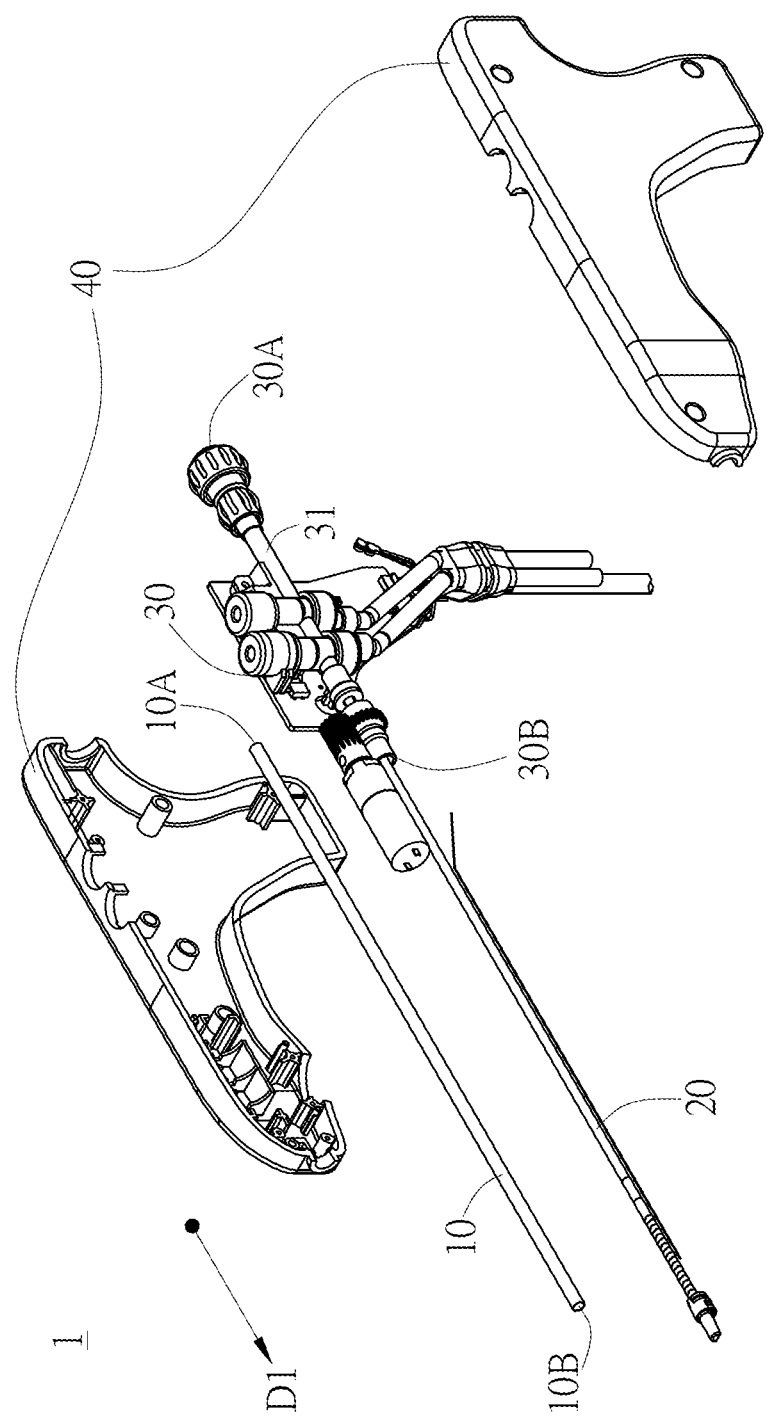
FIG. 1A is an exploded view drawing of an embodiment of the medical device of the present disclosure.
Figure 1B:
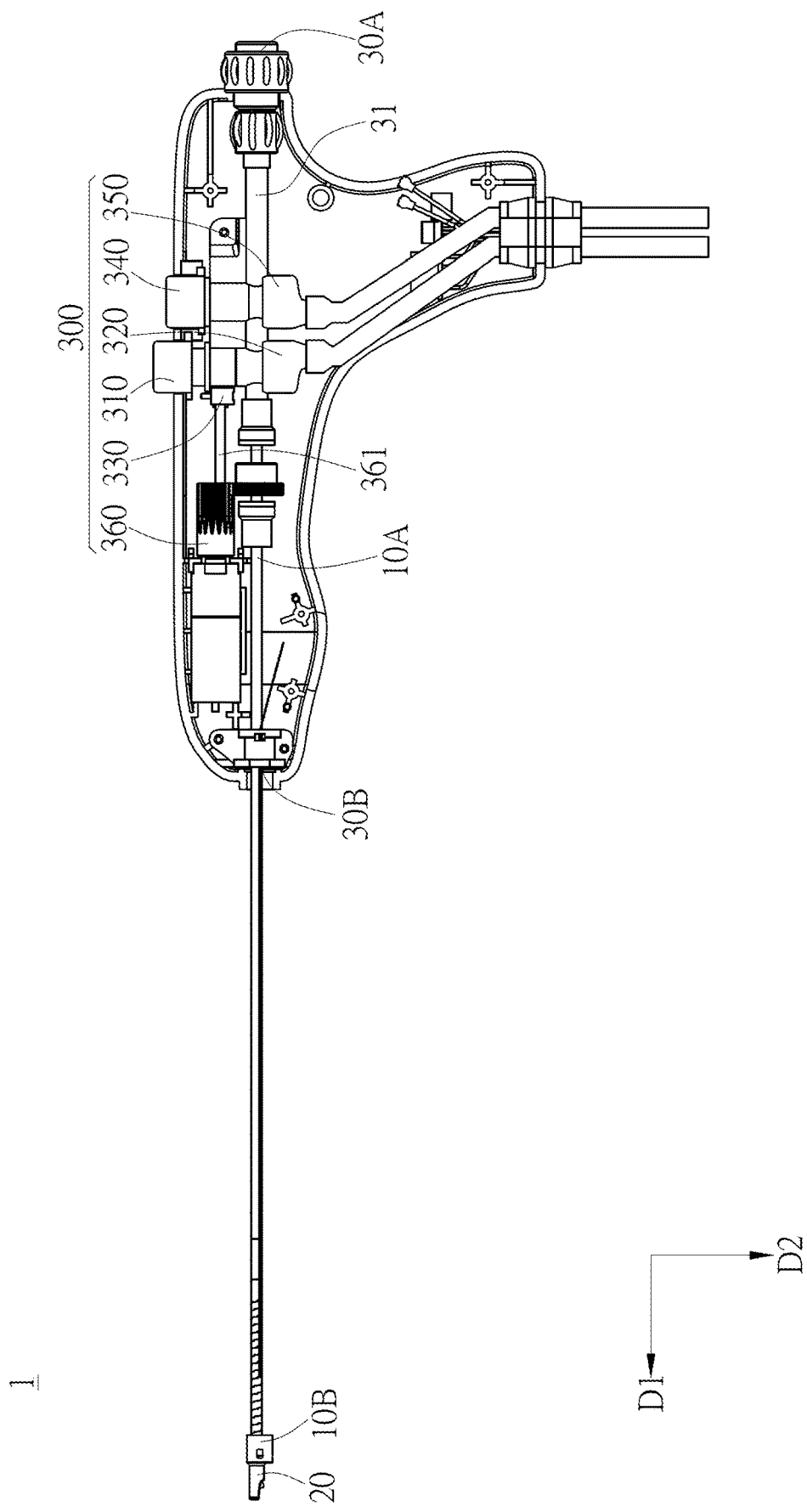
FIG. 1B is a plane diagram of the internal structure of an embodiment of the medical device of the present disclosure.

Please refer to FIG. 1A and FIG. 1B. FIG. 1A and FIG. 1B respectively illustrate an exploded view and a schematic view of the internal structure of a medical device 1 in an embodiment of the present disclosure. As illustrated in FIG. 1A and FIG. 1B, the medical device 1 of the present disclosure includes an outer tube 10, an operation portion 20, a control portion 30 and an outer case 40. The outer tube 10 is configured to extend along a first direction D1 and has a first outer tube end 10A and a second outer tube end 10B opposite to each other. When using the medical device 1, the first outer tube end 10A is relatively adjacent to the operator (proximal), and the second outer tube end 10B is relatively away from the operator (distal). The operation portion 20 is disposed in the outer tube 10 to protrude from the second outer tube end 10B; therefore, when using the medical device 1, at least a portion of the operation portion 20 is located inside the outer tube 10 so as to conduct operations such as resection and debridement on the operation target. For example, in the present embodiment, the operation portion 20 may include a blade to perform debridement.

In the present embodiment, at least a portion of the control portion 30 is located inside an outer case 40. The control portion 30 has a first handle end 30A and a second handle end 30B opposite to each other. When using the medical device 1, the first handle end 30A and the second handle end 30B are respectively adjacent to and away from the operator. A channel 31 is formed between the first handle end 30A and the second handle end 30B, so that the first handle end 30A and the second handle end 30B communicate with each other. The second handle end 30B is coupled to the first outer tube end 10A, so that the channel 31 communicates with the outer tube 10 along the first direction D1.

The control portion 30 includes a control module 300. Furthermore, in the present embodiment, the control module 300 includes at least one suction control portion 310, a suction port actuator 320, a switching unit 330, a flush control portion 340 and a flush port actuator 350. The suction control portion 310 and the flush control portion 340 are adjacent to each other and configured to move along a second direction D2. The switching unit 330 is electrically connected to the operation portion 20 to switch the work status of the operation portion 20 (for example, starting or stopping the work of the operation portion 20). The second direction D2 is a different direction from the first direction D1, for example, it is a direction perpendicular to the first direction D1, but not limited thereto, as long as the tracks for the suction control portion 310 and the flush control portion 340 are intersected with the channel 31. The suction port actuator 320 and the flush port actuator 350 are located opposite to the suction control portion 310 and the flush control portion 340 with the channel 31 therebetween, and the suction control portion 310 and the flush control portion 340 enable the suction port actuator 320 and the flush port actuator 350 to create suction in and flush the channel 31.

Figure 2A:
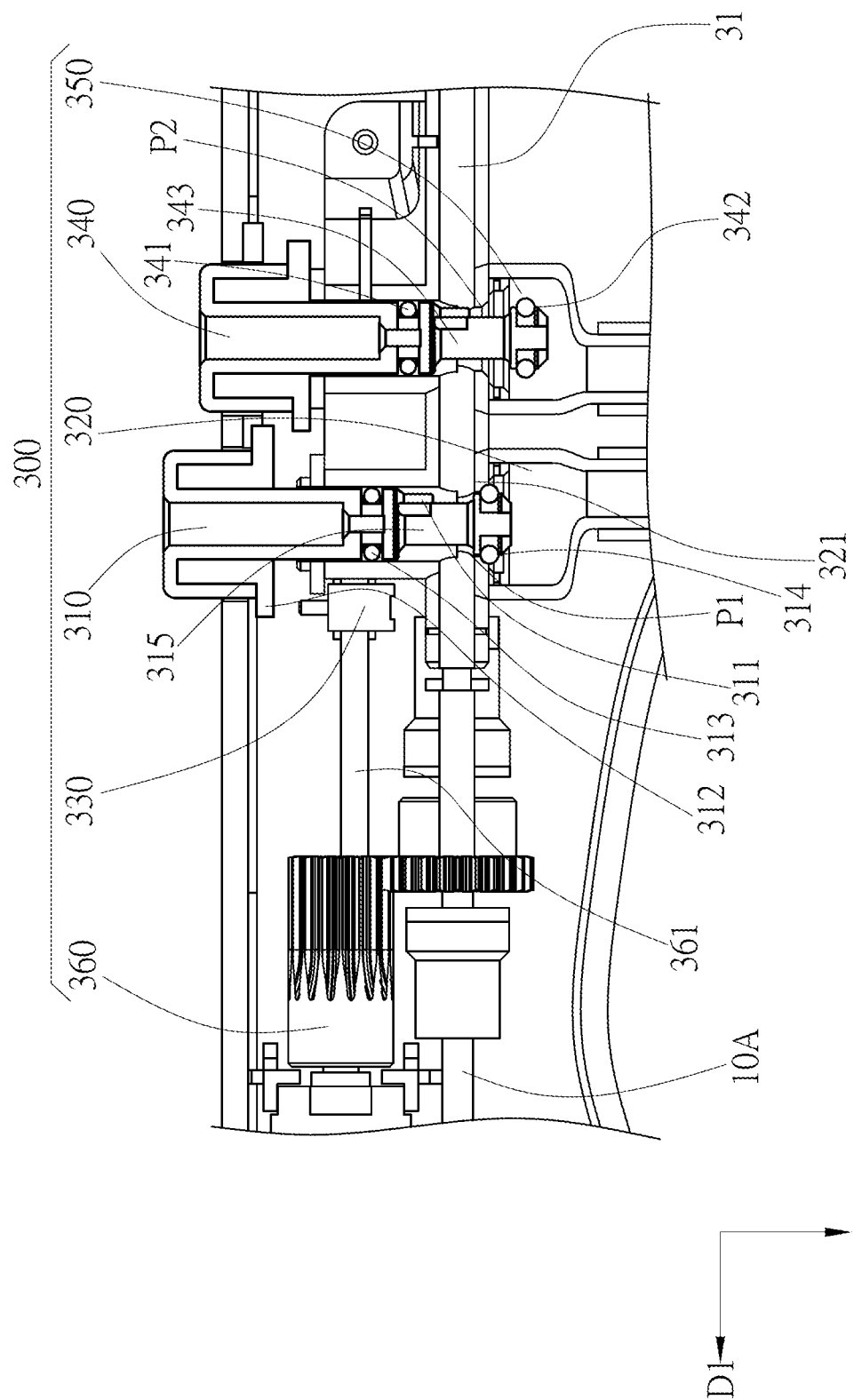
FIG. 2A is a diagram of a partial cross-section of the control portion of an embodiment of the medical device of the present disclosure when the suction control portion is located at the first position.
Figure 2B:
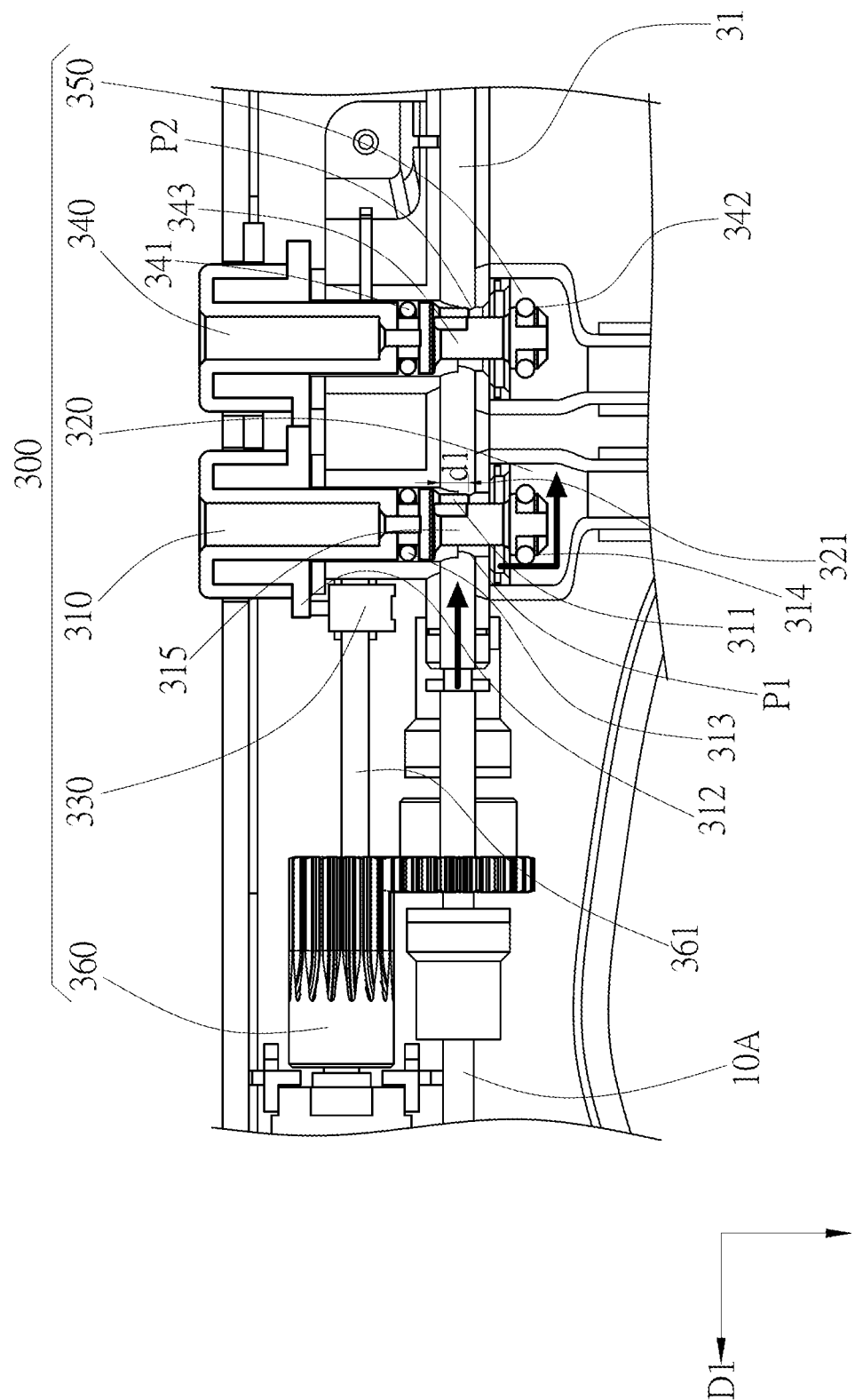
FIG. 2B is a diagram of a partial cross-section of the control portion of an embodiment of the medical device of the present disclosure when the suction control portion is located at the second position.
Figure 2C:
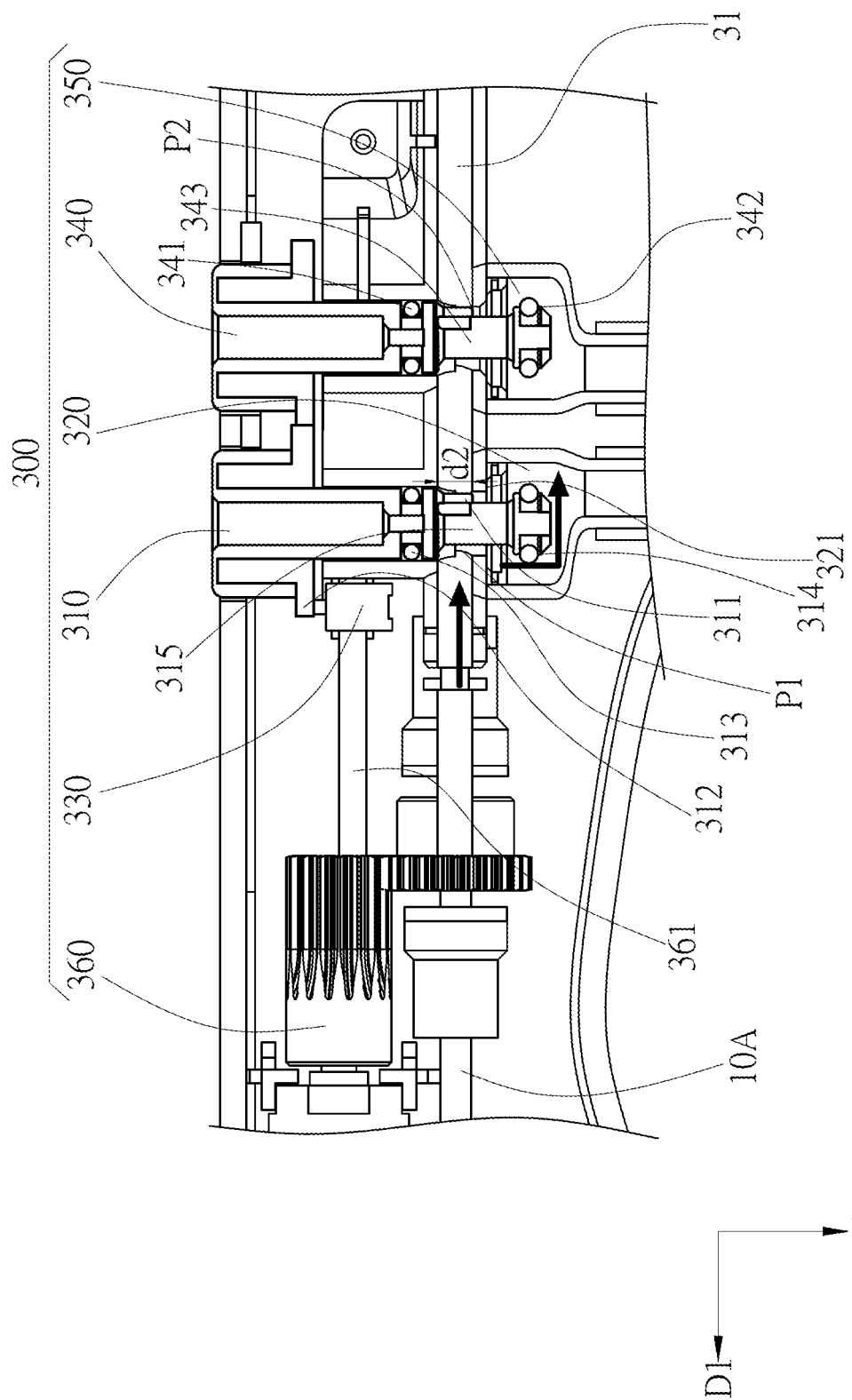
FIG. 2C is a diagram of a partial cross-section of the control portion of an embodiment of the medical device of the present disclosure when the suction control portion is located at the third position.

Please refer to FIG. 2A, FIG. 2B and FIG. 2C. FIG. 2A, FIG. 2B and FIG. 2C are cross-section diagrams respectively illustrating a portion of the control portion 30 of the medical device 1 in an embodiment of the present disclosure when the suction control portion 310 is located at a first position, a second position, and a third position, wherein the first position, the second position and the third position are collinear along the second direction D2 and are sequentially closer to the channel 31. In the present embodiment, as illustrated in FIG. 2A, FIG. 2B and FIG. 2C, the suction control portion 310 has a stopping unit 311 toward the channel 31 (for example, along the second direction D2) and a protruding portion 312 toward a different direction from the stopping unit 311 (for example, along the first direction D1). The protruding portion 312 is preferably collinear with at least a portion of the switching unit 330 along the second direction D2; in other words, the switching unit 330 is located on a passageway on which the protruding portion 312 moves. Therefore, the switching unit 330 can be released and driven by the suction control portion 310 so as to switch the work status of the operation portion 20. However, the switching unit 330 can be activated if at least a portion of the protruding portion 312 is in contact with or presses on the switching unit 330 when the suction control portion 310 moves to the third position (FIG. 2C) along the second direction D2.

In the present embodiment, when the suction control portion 310 is located at the first position (FIG. 2A), the control module 300 is configured to stop the suction port actuator 320 from creating suction in the channel and to make the switching unit 330 stop the operation of the operation portion 20. For example, in the present embodiment, the suction control portion 310 is configured to be at least partially located inside a first channel P1 extending along the second direction D2, and includes an upper O-ring 313, lower O-ring 314 and an extending portion 315 located between the upper O-ring 313 and the lower O-ring 314 and moving along and within the first channel P1. The upper and lower ends of the extending portion 315 are connected to the portions on which the upper O-ring 313 and the lower O-ring 314 are disposed respectively, so as to link up the movements of the upper O-ring 313 and the lower O-ring 314. In addition, the portion of the extending portion 315 configured to pass through the channel 31 is inwardly concaved toward one side or configured to avoid the channel 31 so as to keep the channel 31 unblocked. When the suction control portion 310 is located at the first position (FIG. 2A), the upper O-ring 313 and the wall of the first channel P1 maintain close contact; at the same time, the lower O-ring 314 and the wall of the first channel P1 also maintain close contact so as to keep the suction valve 321 (consisting of the lower O-ring 314 and the wall of the first channel P1) of the suction port actuator 320 closed to stop creating suction in the channel 31.

When the suction control portion 310 is located at the second position (FIG. 2B), the control module 300 is configured to enable the suction port actuator 320 to create suction in the channel 31. For example, the control module 300 is configured to open the suction valve 321 so as to create suction by moving the suction control portion 310 from the first position (FIG. 2A) to the second position (FIG. 2B). And when the suction control portion 310 moves from the second position (FIG. 2B) to the first position (FIG. 2A), by the closing of the suction valve 321, the suction port actuator 320 is stopped to create suction. Furthermore, in the present embodiment, when the suction control portion 310 moves from the first position (FIG. 2A) to the second position (FIG. 2B), since the width of the wall of the first channel P1 located under the channel 31 is widened toward the suction port actuator 320, along with the moving down of the extending portion 315, the contact between the lower O-ring 314 and the wall of the first channel P1 is gradually broken so as to open the suction valve 321. On the other hand, the width of the portion of the first channel P1 located over the channel 31 is quite uniform; therefore, when the suction control portion 310 moves from the first position (FIG. 2A) to the second position (FIG. 2B), the upper O-ring 313 and the wall of the first channel P1 can be kept in contact. In the present embodiment, when the suction control portion 310 is located at the second position (FIG. 2B), the stopping portion 311 may extend to the first depth d1 of the channel 31; however, the present embodiment is not limited thereto. The stopping portion 311 may be outside of the channel 31 in accordance with the actual disposition and location of the stopping portion 311. In addition, in the present disclosure, constructional principles of the suction control portion 310 driving the suction port actuator 320 are not limited thereto, as long as the suction port actuator 320 is configured to be switched on or off in accordance with the position of the suction control portion 310.

In the present embodiment, the flush control portion 340 is at least partially located in the second channel P2 extending along the second direction D2 and in parallel to the first channel P1. In addition, the flush control portion 340 includes an upper O-ring 341, a lower O-ring 342 and an extending portion 343 between the upper O-ring 341 and the lower O-ring 342, moving along the second channel P2. The second channel P2 may have the same or similar structure as the first channel P1; therefore, at the same time when the upper O-ring 341 and the wall of the second channel P2 are kept in close contact, the relative position between the lower O-ring 342 and the wall of the second channel P2 is changed along with the movement of the extending portion 343. The flush port actuator 350 is configured to stop flushing in the channel 31 when the lower O-ring 342 and the wall of the second channel P2 are in close contact, and to enable the flush port actuator 350 to flush in the channel 31 when the close contact between the lower O-ring 342 and the wall of the second channel P2 is broken; however, the designs of the flush control portion 340 and the flush port actuator 350 of the present disclosure are not limited thereto. Different designs of the flush systems can be also applied.

When the suction control portion 310 is located at the third position (please refer to FIG. 2C), the control module 300 is configured to enable the suction port actuator 320 to create suction in the channel 31 and to drive the switching unit 330 to activate the operation portion 20. In addition, the stopping unit 311 at least partially extends into the channel 31. In other words, when another instrument is extended into the channel 31, the stopping portion 311 will be stopped immediately and cannot move down. As a result, the suction control portion 310 cannot move to the third position. Furthermore, in the present embodiment, when the suction control portion 310 is located at the third position (please refer to FIG. 2C), the stopping portion 311 may be extended to a second depth d2 of the channel 31, and the second depth d2 is greater than the first depth d1. Specifically, when the suction control portion 310 moves from the second position (FIG. 2B) to the third position (FIG. 2C), the upper O-ring 313 and the wall of the first channel P1 can be kept in close contact, and the lower O-ring 314 and the wall of the first channel P1 not in close contact. As such, the control module 300 can keep the suction valve 321 open. After the protruding portion 312 is at least partially in contact with the switching unit 330, the switching unit 330 is driven to activate the operation portion 20. For example, as illustrated in FIG. 1B and FIG. 2A-2C, the control module 300 may further include a motor 360 providing power to the operation portion 20 and a cable 361 electrically connecting the motor 360 and the switching unit 330. As such, when the suction control portion 310 is located at the third position (FIG. 2C), the switching unit 330 drives the motor 360 to switch the operation portion 20 to the working status. However, the structure of the suction port actuator 320 and principles of driving the suction port actuator 320 or the switching unit 330 are not limited thereto. For example, the motor 360 and the switching unit 330 may be connected wirelessly or the switching unit 330 may be connected to a driver in the operation portion 20 directly or wirelessly. As long as the driving of the suction port actuator 320 or the switching unit 330 is dependent on the suction port actuator 320, the present disclosure is not limited to the manner of connecting.

Figure 2D:
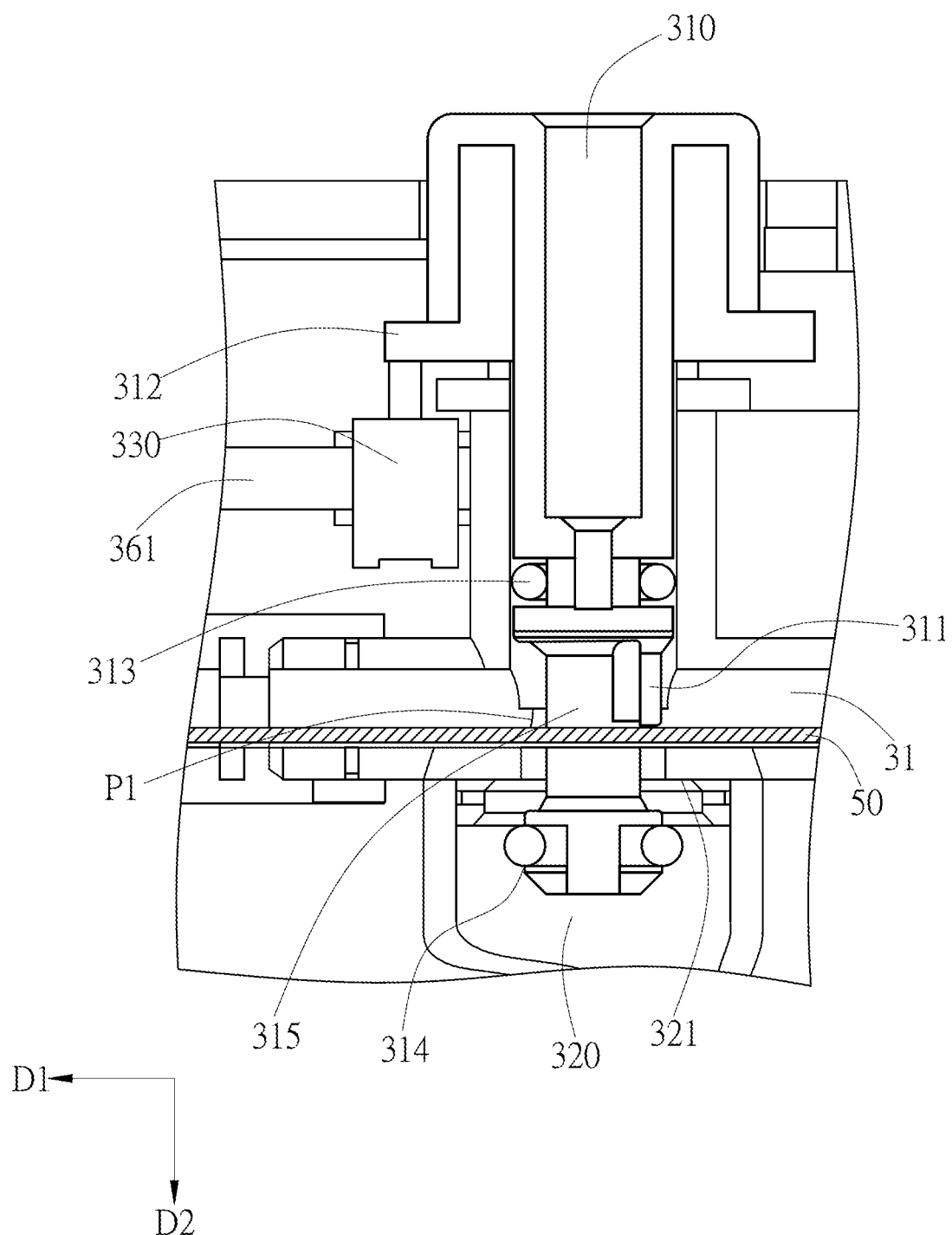
FIG. 2D is a diagram of a stopping unit of an embodiment of the medical device of the present disclosure preventing the suction control portion from moving from the second position to the third position.

Therefore, a single suction port actuator 320 (For example, it can be a button protruding over the medical device 1) may perform tasks such as suction and debridement, and it is very convenient for surgeons to operate. In addition, when the operation portion 20 performs tasks such as debridement, suctioning is still ongoing. Therefore, even if tissues such as brain tissues are bleeding under surgical treatment, good visibility can be ensured by absorbing blood as soon as possible. In addition, since the suction control portion 310 has the stopping unit 311, it is possible to prevent or decrease the chance of the suction control portion 310 moving to the third position unexpectedly (for example, moving to the third position only if the suction control portion 310 is pressed hard), activating the operation portion 20 and damaging the part under surgery or the extended instrument. Furthermore, please refer to FIG. 2D. FIG. 2D illustrates the stopping unit 311 preventing the suction control portion 310 from moving from the second position to the third position in an embodiment of the medical device of the present disclosure. As illustrated in FIG. 2D, when the external instrument 50 is located between the suction control portion 310 and the suction port actuator 320 inside the channel 31, even if someone wants to press the suction control portion 310 to make it move from the second position to the third position, the stopping portion 311 would interfere with the extended external instrument 50, making it not able to move down. Therefore, the suction control portion 310 is prevented from moving to the third position unexpectedly. Related embodiments are further described as below.

Figure 3A:
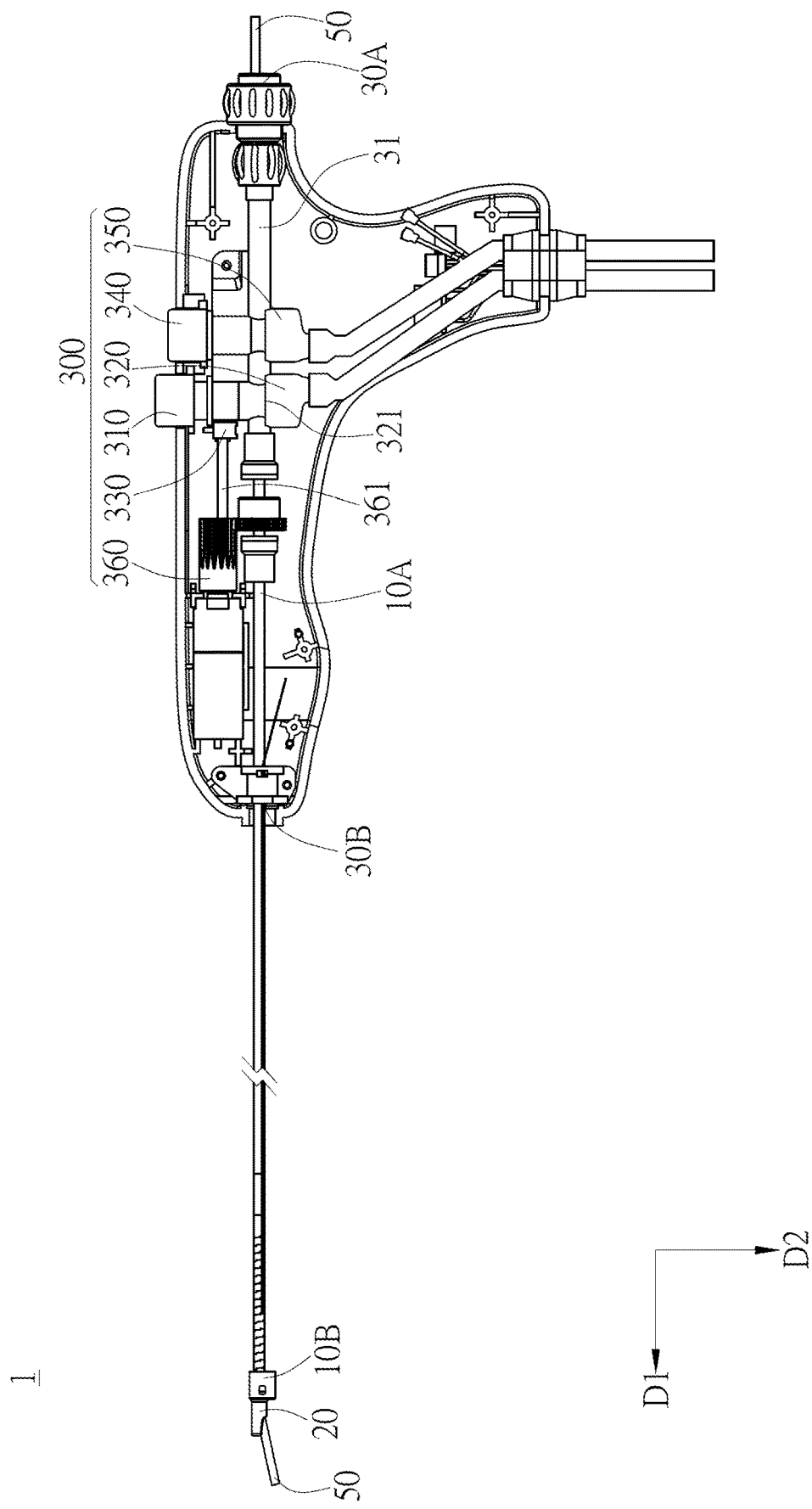
FIG. 3A is a plane diagram of the internal structure of an embodiment of the medical device of the present disclosure when inserting an external instrument.
Figure 3B:
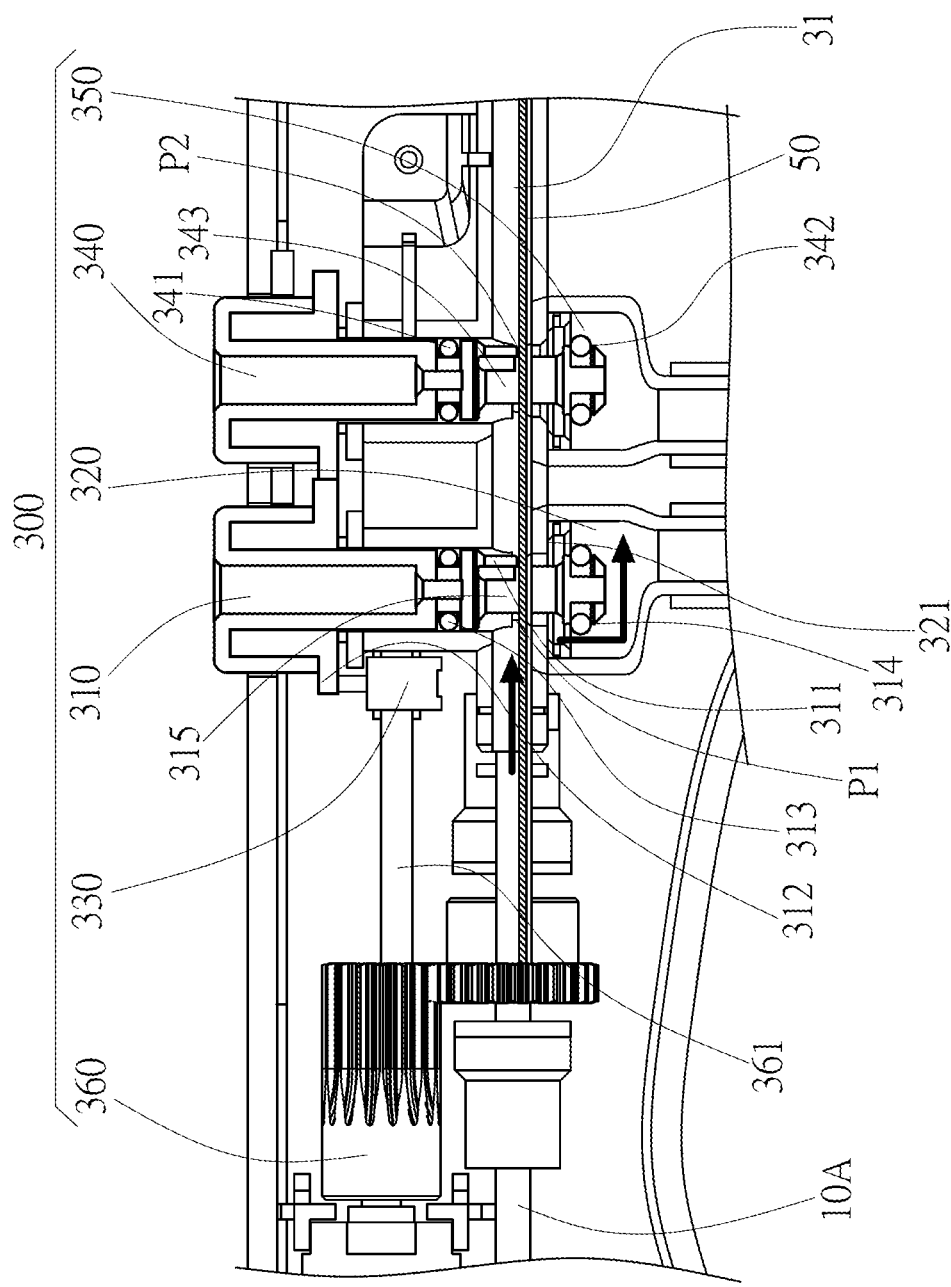
FIG. 3B is a plane diagram of preventing the suction control portion from moving from the second position to the third position when inserting the external instrument.

Please refer to FIG. 3A and FIG. 3B. FIG. 3A illustrates a plane view of the internal structure of an embodiment of the medical device 1 of the present disclosure when an external instrument 50 is inserted, and FIG. 3B illustrates the cross-section view of preventing the suction control portion 310 from moving from the second position (please refer to FIG. 2B) to the third position (please refer to FIG. 2C) when the external instrument 50 is inserted. Specifically, as illustrated in FIG. 3A, the external instrument 50, for example, may be a cautery device (electrosurgical blade), and the length of the external instrument 50 is preferably greater than the length between the first handle end 30A and the second outer tube end 10B (that is, greater than the whole length of the medical device 1 along the first direction D1), so that the external instrument 50 can extend to protrude from the second outer tube end 10B so as to make it convenient for operators to withdraw the external instrument 50 from the first handle end 30A when performing tasks such as cautery. Therefore, when the medical device 1 of the present disclosure and the external instrument 50 are used in a combination, the medical device 1 may include means for suction, flush, debridement, and cautery so as to enhance the efficiency of the surgical tasks; however, the present disclosure is not limited thereto. For example, the external instrument 50 is not limited to a cautery device (electrosurgical blade), and in another embodiment, the flush control portion 340 and the flush port actuator 350 and the like can be omitted in accordance with the actual demand. The medical device 1 of the present disclosure is not limited to the mentioned configuration.

Figure 3D:
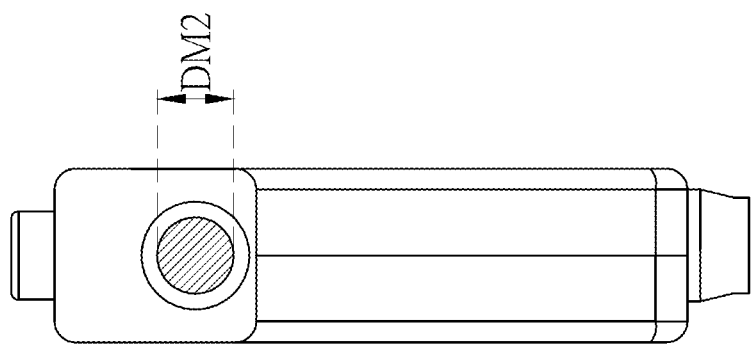
FIG. 3D is a back view of an embodiment of the medical device after inserting the external instrument.
Figure 3C:
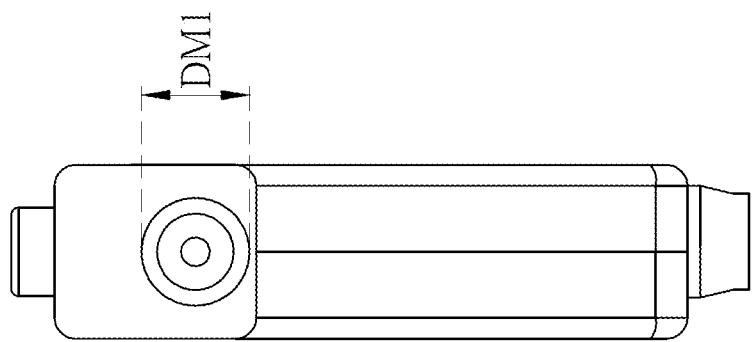
FIG. 3C is a back view of an embodiment of the medical device before inserting the external instrument.

Please refer to FIG. 3C and FIG. 3D. FIG. 3C and FIG. 3D respectively illustrate the back view of an embodiment of the medical device 1 before and after the external instrument 50 is inserted. As illustrated in FIG. 3C, in an embodiment of the present disclosure, the diameter DM1 of the channel 31 ranges from 1.0 mm to 4.0 mm. And as illustrated in FIG. 3D, the diameter DM2 of the external instrument 50 is greater than or equal to 0.5 mm and smaller than the diameter DM1. Furthermore, the diameter DM2 preferably ranges from 0.5 mm to 2.0 mm. In the case of the diameter DM1 ranging from 1.0 mm to 4.0 mm, by inserting an external instrument 50 having a diameter DM2 greater than or equal to 0.5 mm, the stopping unit 311 can be prevented from extending to the second depth d2 of the channel 31 so as to prevent the suction control portion 310 from moving from the second position (please refer to FIG. 2B) to the third position (please refer to FIG. 2C). Therefore, when performing the work of suction only, by inserting the suction control portion 310 into the channel 31, it is possible to further prevent mistakenly activating the operation portion 20 and damaging other tissues or carelessly extending the instruments. However, the present disclosure is not limited thereto. For example, even if the diameter DM1 and the diameter DM2 are not within the abovementioned ranges, it is still possible to prevent the suction control portion 310 from moving from the second position (please refer to FIG. 2B) to the third position (please refer to FIG. 2C) by adjusting the ratio of the diameter DM1 to the diameter DM2.

Specifically, the diameter DM1 of the channel 31 is preferably greater than the diameter DM2 of the external instrument 50 and is preferably smaller than or equal to 8 times the diameter DM2 (that is, the diameter DM2<the diameter DM1≤8×the diameter DM2). The diameter DM1 further preferably equals to 2 times the diameter DM2 (2×the diameter DM2). When the diameter DM1 and the diameter DM2 satisfy the mentioned relationships, it is also possible to prevent the stopping unit 311 from extending to the second depth d2 of the channel 31 to prevent the suction control portion 310 from moving from the second position (please refer to FIG. 2B) to the third position (please refer to FIG. 2C).

Figure 4A:
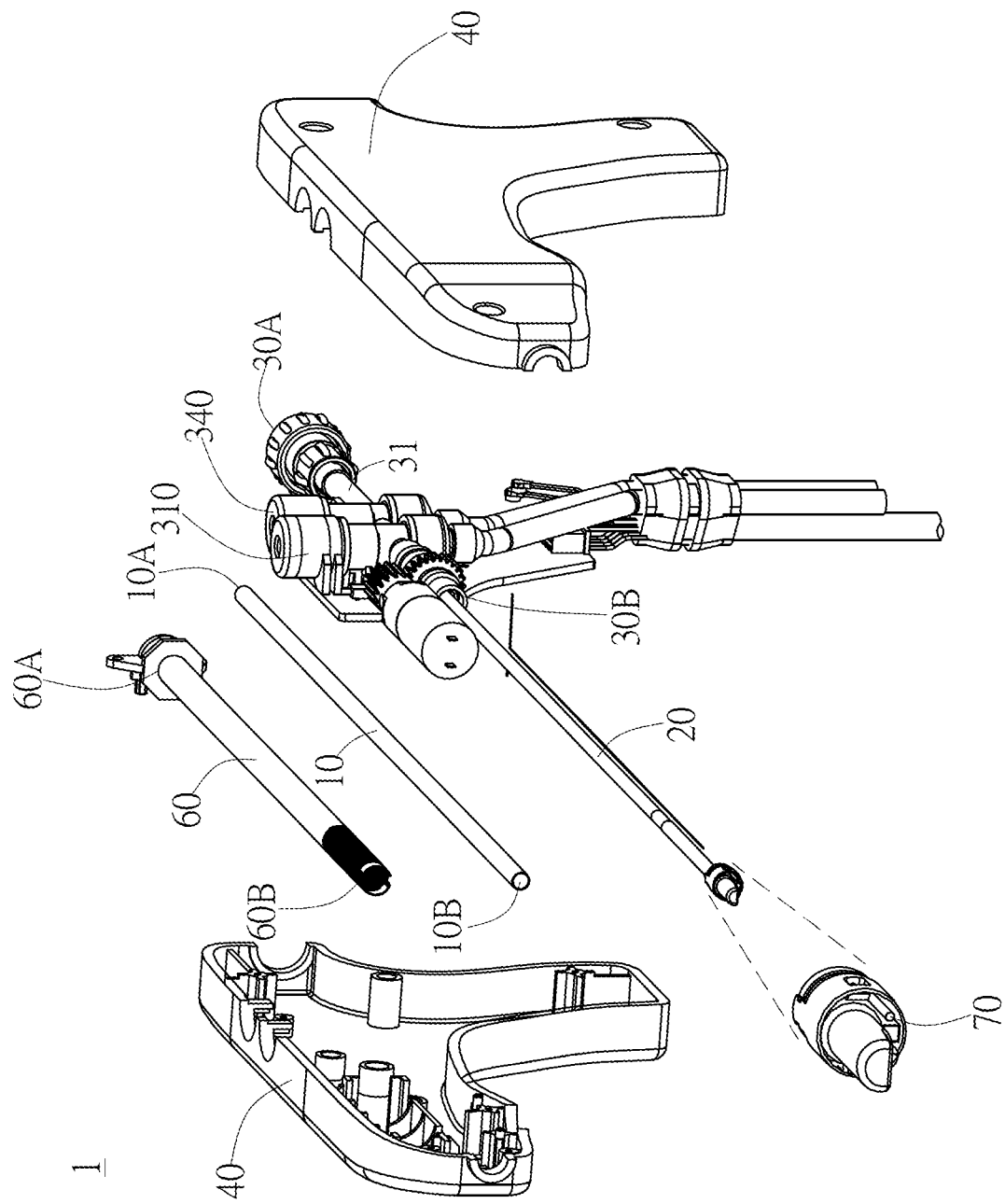
FIG. 4A is an exploded view of a variant embodiment of the medical device.
Figure 4B:
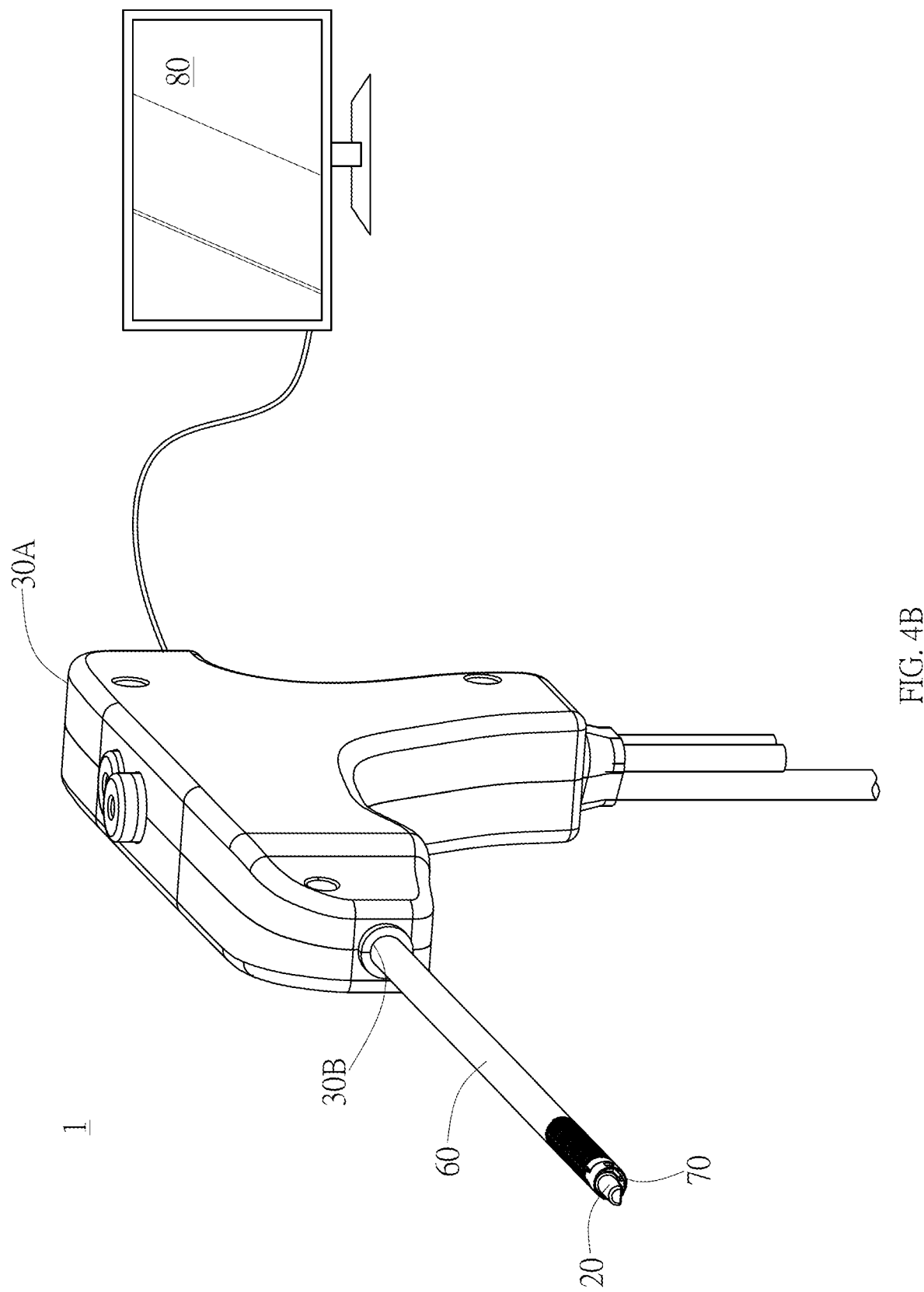
FIG. 4B is a three-dimensional of a variant embodiment of the medical device.

Please refer to FIG. 4A and FIG. 4B. FIG. 4A and FIG. 4B respectively illustrate an exploded view and a three-dimensional diagram of a variant embodiment of the medical device 1. As illustrated in FIG. 4A and FIG. 4B, in the present embodiment, the medical device 1 may optionally include elements such as an introducer 60, an image capture unit 70, and a display device 80. The introducer 60 has a first introducer end 60A and a second introducer end 60B open and opposite to each other. When using the medical device 1, the first introducer end 60A is toward the operator (such as the surgeon) and the second introducer end 60B is toward the patient receiving surgical treatment. The second outer tube end 10B is preferably configured to at least partially protrude from the second introducer end 60B. By disposing the introducer 60, when the medical device 1 is inserted into the patient, it is possible to prevent the medical device 1 from hitting the tissues of the patient and the like.

In addition, the image capture unit 70, for example, may be a camera located at a portion of the operation portion 20 protruding from the second outer tube end 10B so as to capture images along the direction the medical device 1 is introduced. In addition, the display device 80 is operatively coupled to the image capture unit 70 so as to display the image captured by the image capture unit 70 at real time. By disposing the image capture unit 70 and the display device 80, the relative locations of the medical device 1 and the patient's tissues can be confirmed when the operator inserts the medical device 1. In addition, when the operation portion 20 is activated or suction is performed, the status of the patient such as bleeding or blood being drawn can also be confirmed. The display device 80 is preferably a display device with high resolution; furthermore, it preferably has a function such as voice guidance. However, the present disclosure is not limited thereto.

In summary, according to the medical device of the present disclosure, the work of debridement and suction can be performed at the same time based on the structure of the channel connected with the operation portion so as to ensure good visibility in the process of surgery. At the same time, when combined with an external device such as a cautery device and the operation portion is confirmed to have stopped, it is also possible to perform cautery and suction at the same time, or suction only.

The aforementioned description merely represents preferred embodiments of the present disclosure. It should be noted that various changes and modifications of the present disclosure are allowed without departing from the concepts and principles of the present disclosure. People skilled in the art should understand the present disclosure is limited by claims and various equivalent alternation based on the specification and FIGs are consequently viewed as being embraced by the scope of the present disclosure.

What is claimed is:

1. A medical device, comprising: an outer tube; an operation portion at least partially located inside the outer tube; and a control portion having a channel communicating with the outer tube along a first direction, the control portion including a control module, wherein the control module includes: at least one suction control portion having a stopping unit facing the channel, wherein the suction control portion is configured to move along a second direction different from the first direction; a suction port actuator located opposite to the suction control portion with the channel therebetween and driven by the suction control portion; a switching unit configured to be driven by releasing the suction control portion to switch a working status of the operation portion, wherein; when the suction control portion is located at a first position, the control module is configured to stop the suction port actuator creating suction in the channel and the switching unit is configured to stop a movement of the operation portion; when the suction control portion is located at a second position, the control module is configured to enable the suction port actuator to create suction in the channel; and when the suction control portion is located at a third position, the control module is configured to enable the suction port actuator to create suction in the channel and to enable the switching unit to activate the operation portion, and the stopping unit at least partially extends into the channel.

2. The medical device according to claim 1, further including a suction valve, wherein when the suction control portion is located at the second position, the control module is configured to open the suction valve to create suction in the channel.

3. The medical device according to claim 1, wherein when the suction control portion is located at the second position, the stopping unit at least partially extends into the channel,
   wherein the stopping unit extends to a first depth of the channel when the suction control portion is located at the second position,
   wherein the stopping unit extends to a second depth of the channel when the suction control portion is located at the third position,
   wherein the second depth is larger than the first depth.

4. The medical device according to claim 1, wherein the control module further includes:
   a flush control portion configured to move along the second direction; and
   a flush port actuator opposite the flush control portion with the channel therebetween and enabled to flush the channel by the flush control portion.

5. The medical device according to claim 1, further comprising an external instrument, the external instrument at least partially located between the at least one suction control portion and the suction port actuator.

6. The medical device according to claim 1, further comprising; an image capture unit located at a portion of the operation portion protruding from the second outer tube end; and a display device workably coupled to the image capture unit e to receive an image captured by the image capture unit and to display the image.

7. The medical device according to claim 1, wherein the control module further includes a motor electrically connected to the switching unit through a cable, and
   wherein when the suction control portion is located at the third position, the switching unit is configured to activate the motor to switch the operation portion to active status.

8. The medical device according to claim 1, further comprising an introducer, the introducer having a first introducer end and a second introducer end that are open and opposite to each other, wherein at least a portion of the second outer tube end protrudes from the second introducer end.

9. The medical device according to claim 1, wherein a diameter of the channel is larger than a diameter of an external instrument and is smaller than or equals to 8 times the diameter of the external instrument.

10. The medical device according to claim 9, wherein the diameter of the channel equals 2 times the diameter of the external instrument.

11. The medical device according to claim 10, wherein the diameter of the external instrument ranges from 0.5 mm to 2.0 mm.

12. The medical device according to claim 9, wherein the diameter of the external instrument is larger than or equal to 0.5 mm and is smaller than the diameter of the channel.

13. The medical device according to claim 1, wherein a diameter of the channel ranges from 1.0 mm to 4.0 mm.

* * * * *